United States Patent
Marshall et al.

(10) Patent No.: US 12,163,167 B2
(45) Date of Patent: Dec. 10, 2024

(54) METHODS AND COMPOSITIONS FOR REDUCING BACTERIAL LOAD IN TOBACCO

(71) Applicant: R.J. Reynolds Tobacco Company, Winston-Salem, NC (US)

(72) Inventors: Jerry Wayne Marshall, Stokesdale, NC (US); Anthony Richard Gerardi, Winston-Salem, NC (US)

(73) Assignee: R.J. Reynolds Tobacco Company, Winston-Salem, NC (US)

(*) Notice: Subject to any disclaimer, the term of this patent is extended or adjusted under 35 U.S.C. 154(b) by 201 days.

(21) Appl. No.: 17/665,968

(22) Filed: Feb. 7, 2022

(65) Prior Publication Data
US 2022/0162577 A1 May 26, 2022

Related U.S. Application Data

(62) Division of application No. 16/294,214, filed on Mar. 6, 2019, now abandoned.

(60) Provisional application No. 62/639,679, filed on Mar. 7, 2018.

(51) Int. Cl.
| | |
|---|---|
| *C12N 9/36* | (2006.01) |
| *A01N 63/50* | (2020.01) |
| *A24B 15/18* | (2006.01) |
| *A24B 15/20* | (2006.01) |
| *A24B 15/30* | (2006.01) |
| *C12N 15/74* | (2006.01) |
| *C12N 15/82* | (2006.01) |

(52) U.S. Cl.
CPC ........... *C12N 9/2462* (2013.01); *A01N 63/50* (2020.01); *A24B 15/183* (2013.01); *A24B 15/20* (2013.01); *A24B 15/307* (2013.01); *C12N 15/746* (2013.01); *C12N 15/8243* (2013.01); *C12N 15/8281* (2013.01); *C12Y 302/01017* (2013.01)

(58) Field of Classification Search
CPC .................................................. C12N 9/2462
See application file for complete search history.

(56) References Cited

U.S. PATENT DOCUMENTS 10,407,472 B2 * 9/2019 Thompson ............... C09K 8/62
2015/0252380 A1 9/2015 Gabriel et al.

FOREIGN PATENT DOCUMENTS

WO WO 2016/123425 A1 8/2016

OTHER PUBLICATIONS

Gill, J., et anan, "Bacteriophage Ecology and Plants," APSnet Feature Story, 2003, pp. 1-17.
Kovalskaya, N., et al., "Antimicrobial Activity of Bacteriophage Endolysin Produced in *Nicotiana benthamiana* Plants," *J. Microbiol. Biotechnol.*, 2016, vol. 26(1), pp. 160-170.
Starkevič, U, et al., "High-yield production of a functional bacteriophage lysin with antipneumococcal activity using a plant virus-based expression system," Journal of Biotechnology, 2015, vol. 200, pp. 10-16.

* cited by examiner

*Primary Examiner* — Suzanne M Noakes
(74) *Attorney, Agent, or Firm* — Womble Bond Dickinson (US) LLP

(57) ABSTRACT

Methods and compositions are provided for expressing an endolysin in a bacterium or in a tobacco plant or plant part. Expression of the endolysin can reduce the total bacterial load on the plant and in tobacco products produced from the plant. Accordingly, the level of tobacco specific nitrosamines (TSNA) in a cured tobacco product can be decreased when the tobacco leaves used in the product were harvested from a plant expressing endolysin or when bacteria modified to express endolysin is used to treat the tobacco. Thus, bacteria and tobacco plants and plant parts are provided that express an endolysin. Further provided are methods for decreasing the microbial load on a tobacco plant and in a tobacco product by applying a solution of bacteria modified to express an endolysin or by modifying a tobacco plant to express endolysins. Smokeless tobacco products including such modified tobacco plant parts are also provided.

9 Claims, No Drawings

METHODS AND COMPOSITIONS FOR REDUCING BACTERIAL LOAD IN TOBACCO

CROSS-REFERENCE TO RELATED APPLICATIONS

This application is a divisional of U.S. application Ser. No. 16/294,214, filed Mar. 6, 2019, which claims priority from U.S. Provisional Application No. 62/639,679, filed Mar. 7, 2018, which applications are hereby incorporated in their entirety by reference in this application.

FIELD OF THE INVENTION

The present disclosure relates to products made or derived from tobacco, or that otherwise incorporate tobacco, and are intended for human consumption. In particular, the invention is drawn to methods and compositions for reducing bacterial load in tobacco plants and products.

BACKGROUND

Cigarettes, cigars, and pipes are popular smoking articles that employ tobacco in various forms. Such smoking articles are employed by heating or burning tobacco to generate aerosol (e.g., smoke) that may be inhaled by the smoker. Tobacco may also be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Breslin et al.; US Pat. Pub. Nos. 2004/0020503 to Williams; 2005/0115580 to Quinter et al.; 2005/0244521 to Strickland et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; and 2009/0293889 to Kumar et al.; PCT WO 04/095959 to Arnarp et al.; and U.S. patent application Ser. No. 12/638,394, filed Dec. 15, 2009, to Mua et al. (now published as US 2011/0139164 to Mua et al.); each of which is incorporated herein by reference. Exemplary smokeless tobacco products include CAMEL Snus, CAMEL Orbs, CAMEL Strips and CAMEL Sticks by R. J. Reynolds Tobacco Company; REVEL Mint Tobacco Packs and SKOAL Snus by U.S. Smokeless Tobacco Company; and MARLBORO Snus and Taboka by Philip Morris USA.

As the name implies, smokeless tobacco products are consumed without smoking (heating), which could lead to greater potential for the consumer to be exposed to viable microorganisms or their metabolites during use, if the product contains microorganisms, such as the microorganisms commonly found on tobacco plants.

The present invention provides methods and compositions for reducing bacterial load in tobacco plants and tobacco products. In some aspects of the invention, modified tobacco plant having endolysin activity, including plant parts and plant cells, are provided. In other aspects of the invention, fermentation processes and inoculants with endolysin activity are provided.

SUMMARY OF THE DISCLOSURE

The present disclosure provides compositions and methods for the expression of endolysins in tobacco plants, tobacco plant parts, and tobacco cells. The tobacco plants and plant parts disclosed herein comprise a heterologous nucleic acid molecule comprising a nucleotide sequence encoding an endolysin or other membrane-disrupting enzyme. In one aspect, a tobacco plant, plant part, or plant cell is provided comprising a heterologous nucleic acid molecule comprising nucleic acid sequence encoding an endolysin operably linked to a promoter active in the tobacco plant, plant part, or plant cell. The nucleic acid molecule can be located on an expression construct and/or on a vector. In certain aspects, the nucleic acid molecule is integrated into the genome of said tobacco plant, plant part, or plant cell. In certain aspects, the promoter can be a constitutive promoter, an inducible promoter, a tissue-preferred promoter, a cell type-preferred promoter, or a developmentally-preferred promoter. For example, the nucleic acid sequence encoding the endolysin can be operably linked to a leaf-preferred or stem-preferred promoter. In some aspects, a tobacco plant, plant part, or plant cell is provided, wherein an endolysin is expressed in the leaf of said tobacco plant or plant part. The endolysin expressed in the tobacco plant, plant part, or plant cell can be specific or preferred for Gram-positive bacteria or Gram-negative bacteria.

In some aspects, a seed produced from a tobacco plant modified to express an endolysin is provided. The seed can comprise a nucleic acid molecule comprising the nucleic acid sequence encoding an endolysin. A tobacco product is provided that is produced from a tobacco plant or plant part that expresses an endolysin. The tobacco product can be leaf tobacco, shredded tobacco, cut tobacco, ground tobacco, powder tobacco, tobacco extract, nicotine extract, smokeless tobacco, moist or dry snuff, kretek, pipe tobacco, cigar tobacco, cigarillo tobacco, cigarette tobacco, chewing tobacco, bidis, bits, cigarette, cigarillo, a non-ventilated recess filter cigarette, a vented recess filter cigarette, a cigar, and tobacco-containing gum, lozenges, patches, electronic cigarettes, or any combination thereof. For example, the tobacco product can be a smokeless tobacco product. In some aspects, the tobacco specific nitrosamines (TSNA) content of said tobacco product is at least 10% lower than the TSNA content of a control tobacco product produced solely from tobacco plants not expressing an endolysin.

In one aspect, a method of producing a tobacco plant, plant part, or plant cell expressing an endolysin is provided. Such methods comprise introducing into the tobacco plant, plant part, or plant cell a heterologous nucleic acid molecule comprising a nucleic acid sequence encoding an endolysin operably linked to a promoter active in said tobacco plant, plant part, or plant cell, wherein the endolysin is expressed from the nucleic acid sequence following introduction of said nucleic acid sequence into the tobacco plant, plant part, or plant cell. The nucleic acid molecule can be introduced into the tobacco plant, plant part, or plant cell on a vector, a bacterial cell, a virus, or a bacteriophage. In some aspects, the nucleic acid molecule is stably incorporated into the genome of said tobacco plant, plant part, or plant cell. The endolysin can be expressed in the leaf of the tobacco plant or plant part.

In some aspects, methods are provided for reducing the bacterial load on a tobacco plant or plant part by introducing into the tobacco plant, plant part, or plant cell a heterologous nucleic acid molecule comprising a nucleic acid sequence encoding an endolysin operably linked to a promoter active in the tobacco plant, plant part, or plant cell, wherein the endolysin is expressed from the nucleic acid sequence following introduction of the nucleic acid molecule into the tobacco plant, plant part, or plant cell, and wherein the endolysin reduces the bacterial load on said tobacco plant or plant part. In such methods, the nucleic acid sequence can be introduced into the tobacco plant, plant part, or plant cell on a vector, a bacterial cell, a virus or bacteriophage. In certain aspects of the method, the nucleic acid molecule is stably incorporated into the genome of said tobacco plant, plant part, or plant cell. In some aspects of the method, the endolysin is expressed in the leaf of said tobacco plant or plant part. Expression of an endolysin in a tobacco plant or plant part can reduce the level of at least one species of Gram positive bacteria or Gram negative bacteria. For example, expression of an endolysin can reduce the level of at least one species of *Bacillus, Staphylococcus, Geobacillus, Tetragenococcus, Corynebacterium, Clostridium, Enterococcus, Lactobacillus, Halomonas, Acinetobacter, Burkholderia, Campylobacter, Klebsiella*, or *Pseudomonas*. Specifically, expression of an endolysin can reduce the level of *B. licheniformis, B. pumilus, B. subtilis*, or *S. hominis*.

In certain aspects, a genetically modified bacterium is provided comprising a heterologous nucleic acid molecule comprising a nucleic acid sequence encoding an endolysin, wherein the nucleic acid sequence is operably linked to a promoter active in said genetically modified bacterium. The nucleic acid molecule can be located on a vector or integrated into the genome of the bacterium. In certain aspects, the promoter can be a constitutive promoter, an inducible promoter, a tissue-preferred promoter, a cell type-preferred promoter, or a developmentally-preferred promoter. For example, the nucleic acid sequence encoding the endolysin can be operably linked to a leaf-preferred or stem-preferred promoter. The genetically modified bacterium can be a Gram positive bacterium, such as a lactic acid bacterium. In some embodiments, the expressed endolysin is secreted from the bacterium. The genetically modified bacterium can be provided in a solution.

In some aspects, a method of reducing the bacterial load on a tobacco plant, plant part, or plant cell is provided comprising applying to the tobacco plant or plant part a solution comprising a genetically modified bacterium comprising a heterologous nucleic acid molecule comprising nucleic acid sequence encoding an endolysin, wherein the nucleic acid sequence is operably linked to a promoter active in said bacterium, wherein the bacterium expresses the endolysin, and wherein the expressed endolysin reduces the bacterial load on the tobacco plant or plant part compared to a control plant or plant part. The nucleic acid molecule can be located on a vector or integrated into the genome of the bacterium. In certain aspects, the promoter can be a constitutive promoter, an inducible promoter, a tissue-preferred promoter, a cell type-preferred promoter, or a developmentally-preferred promoter. For example, the nucleic acid sequence encoding the endolysin can be operably linked to a leaf-preferred or stem-preferred promoter. The genetically modified bacterium can be a Gram positive bacterium, such as a lactic acid bacterium, such as a Tetragenococcus bacterium. Expression of an endolysin from the bacterium applied to the plant or plant part can reduce the level of at least one species of Gram positive bacteria or Gram negative bacteria. For example, expression of an endolysin can reduce the level of at least one species of *Bacillus, Staphylococcus, Geobacillus, Tetragenococcus, Corynebacterium, Clostridium, Enterococcus, Lactobacillus, Halomonas, Acinetobacter, Burkholderia, Campylobacter, Klebsiella*, or *Pseudomonas*. Specifically, expression of an endolysin can reduce the level of *B. licheniformis, B. pumilus* or *B. subtilis*, or *S. hominis*. A solution comprising the bacterium modified to express an endolysin can be applied to a live tobacco plant or plant part in the field, or a harvested tobacco plant or plant part prior to or during curing or prior to or during fermentation. In some aspects a tobacco product is produced from the tobacco plant or plant part treated with the genetically modified bacterium.

DETAILED DESCRIPTION

The present disclosure now will be described more fully hereinafter. The disclosure may be embodied in many different forms and should not be construed as limited to the aspects set forth herein; rather, these aspects are provided so that this disclosure will satisfy applicable legal requirements. Like numbers refer to like elements throughout. As used in this specification and the claims, the singular forms "a," "an," and "the" include plural referents unless the context clearly dictates otherwise.

The disclosure provides compositions and methods for the expression of endolysins in tobacco plants, tobacco plant parts, tobacco cells, and bacteria. Various types of agents having bactericidal or bacteriostatic activity are known, e.g. antibiotics, endolysins, antimicrobial peptides and defensins. Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. Endolysins may be divided into five classes: (1) N-acetylmuramidases (lysozymes), (2) endo β-N-acetylglucosaminidases, and (3) lytic transglycosylases, which all cleave the sugar moiety of peptidoglycan, (4) endopeptidases, which cleave the peptide moiety, and (5) N-actylmuramoyl-L-alanine amidases, which cut the amide bond between sugar backbone and peptide linkers. Endolysins show a modular organization exhibiting a combination of different polypeptide domains showing enzymatic activity or cell binding activity, the so-called EADs (enzymatically active domains) and CBDs (cell binding domains), respectively. Mostly, EADs are located at the N-terminal part of the endolysins, and CBDs at the C-terminal parts, but there are also exceptions of this rule of thumb. It is also shown that modules can be exchanged between different cell wall lytic enzymes producing new functional enzymes, which sometimes exhibit even new functional properties (Diaz et al., 1990; Croux et al., 1993; Donovan et al., 2006).

As used herein, the term "endolysin" refers to any enzyme capable of hydrolyzing bacterial cell walls. In particular embodiments, endolysins are capable of depolymerization of the murein or peptidoglycan cell wall. The term includes: 1) glucosaminidases (lysozymes) that attack the glycosidic linkages between the amino sugars of the peptidoglycan; 2) amidases that attack the N-acetylmuramoyl-L-alanine amide linkage between the glycan strand and the cross-linking peptide, and 3) endopeptidases that attack the interpeptide bridge linkages. Accordingly, endolysin activity includes but is not limited to the following activities: endopeptidase, N-acetyl-muramoyl-L-alanine-amidase (amidase), N-acetyl-muramidase, N-acetyl-glucosaminidase (lysozyme) or transglycosylases activity. In some embodiments endolysins are synthesized without an export signal sequence that would permit them access to the peptidoglycan (murein) layer, and they therefore can accumulate in the cytoplasm of phage infected bacteria until they are released by the activity of holins. Endolysin activity can be measured by any method known in the art, including, but not limited to, turbidity reduction assays, zymogram assays, minimum inhibitory concentration (MIC) and minimum bactericidal concentration (MBC) assays, plate lysis, and soft agar overlay assay.

Endolysins may contain also regions which are enzymatically inactive, and bind to the cell wall of the host bacteria, the so-called CBDs (cell wall binding domains). The term "cell wall" as used herein refers to all components that form the outer cell enclosure of the Gram-positive and Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes. The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module. The term "EAD" is used herein synonymously with the term "catalytic domain".

In addition to endolysins, any protein or nucleic acid can be expressed in a tobacco plant or bacterial inoculant that is capable of reducing the bacterial load in a tobacco product. For example, exolysins, autolysins, and bacteriocins, or any other membrane-disrupting enzymes, can be expressed from tobacco plants or bacteria according to the methods disclosed herein. "Exolysins," as used herein refers to enzymes secreted by a bacterial cell that function to lyse the peptidoglycan layer of a different bacterial strain or species. The term "autolysins" as used herein refers to enzymes related to endolysins but encoded by bacteria and involved in e.g. cell division and cell wall metabolism. The term "bacteriocin" as used herein refers to protein-like, polypeptide-like or peptide-like substances which are able to inhibit the growth of other bacteria. Some bacteriocins are capable of degrading bacterial cell walls like Lysostaphin (degrading Staphylococcal cell walls), Mutanolysin (degrading Streptococcal cell walls) and Enterolysin (degrading Enterococcal cell walls). Preferably said inhibition is specifically by means of absorption of said other bacteria to specific receptors of the bacteriocin. In general, bacteriocins are produced by microorganisms. However, the term "bacteriocin" as used herein refers both to an isolated form produced by a microorganism or to a synthetically produced form, and refers also to variants which substantially retain the activities of their parent bacteriocins, but whose sequences have been altered by insertion or deletion of one or more amino acid residues.

Endolysins may be divided into five classes: (1) N-acetylmuramidases (lysozymes), (2) endo-β-N-acetylglucosaminidases, and (3) lytic transglycosylases, which all cleave the sugar moiety of peptidoglycan, (4) endopeptidases, which cleave the peptide moiety, and (5) N-actylmuramoyl-L-alanine amidases, which cut the amide bond between sugar backbone and peptide linkers. Endolysins for expression in tobacco plants (Nicotiana spp.) disclosed herein include but are not limited to LysK, endolysins of the Pseudomonas aeruginosa phages ΦKZ and EL, of the Pseudomonas putida phage OBP, of the phage LUZ24, or from T4 lysozyme, gp61 muramidase, phage Lambda endolysin and gp144 from ΦKZ phage, PSP3 endolysin, of the Salmonella phage, of the Acinetobacter baumannii phage, of the E. coli Phage P2, of the E. coli phage N4 and KIF, of the Salmonella typhimurium phage, Listeria phage endolysins PlyA118, PlyA500, PlyPSA, PlyA511, PlyP35, PlyP40, Staphylococcal phage Phi 11 endolysin, Phi MRU endolysin, Ply 2638, Clostridium perfringens PlyS6, Ply3626, Clostridium difficile: CD27L endolysin, Streptococcus: B30 endolysin, phage Dp-1 Pal amidase, CI endolysin, Cpl-1 endolysin, PlyGBS, Enterococccus: PlyV12, Bacillus anthracis: Phage gamma endolysin PlyG, Lysteria phage endolysins Ply511, PlyPSA, Ply500, and Ply118, Propionibacterium phage endolysin PA6-gp20. In specific embodiments, the endolysin is disclosed in U.S. Patent Application Publication No. 20160219925.

Autolysins for use in the methods and compositions disclosed herein are described in: Bacterial peptidoglycan (murein) hydrolases. Vollmer W, et al. *FEMS Microbiol Rev.* (2008) March; 32(2):259-86. An example of a preferred autolysin is the AtlA Autolysine. Bacteriocins for use in the methods and compositions disclosed herein include Lysostaphin (degrading *Staphylococcus* cell walls), Mutanolysin (degrading *Streptococcus* cell walls) and Enterolysin (degrading *Enterococcus* cell walls).

Endolysins can be expressed as fusion proteins in the transgenic tobacco plants or bacteria described herein. For example, such fusion proteins can comprise an endolysin, an autolysin, or a bacteriocin fused to a peptide with lipopolysachharide (LPS) activity or other membrane disrupting activity. LPS is a major component of the outer membrane of Gram-negative bacteria. The LPS layer increases the negative charge of the cell membrane and protects the membrane from certain kinds of chemical attack. The LPS can be disrupted by peptides having a LPS disrupting activity as e.g. positively charged peptides. Moreover, such peptides may be involved in the outer membrane protein transport mechanism, a destabilization of structural outer membrane proteins and/or in lipid-dependent destabilization.

Compositions provided herein include recombinant nucleic acid constructs for expression of endolysins or other membrane-disrupting enzymes disclosed herein. Expression constructs or expression cassettes can express a single heterologous nucleic acid encoding an endolysin or other membrane-disrupting enzyme or multiple nucleic acids. Likewise, plants and bacteria disclosed herein can comprise a single expression construct for expression of a single nucleic acid, a single expression construct for expression of multiple nucleic acids encoding an endolysin or other membrane-disrupting enzyme, multiple expression constructs each expressing a single nucleic acid, or a combination of expression constructs expressing a single nucleic acid and multiple nucleic acids (e.g., two, three, four, five, or more nucleic acids).

The term "heterologous" according to the present invention when used in reference to a sequence is intended to mean a sequence that originates from a species other than the species in which it is to be expressed, or, if from the same species as the species in which it is to be expressed, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a species other than the species in which it is to be expressed, or, if from the same species as the species in which it is to be expressed, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. In specific embodiments, the nucleic acid molecule comprising a nucleic acid sequence encoding an endolysin or other membrane-disrupting enzyme is heterologous to the tobacco plant, plant part, or plant cell into which the molecule is introduced.

The expression constructs disclosed herein can comprise a heterologous promoter operably linked to a nucleic acid sequence encoding an endolysin or other membrane-disrupting enzyme. The term "operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Furthermore, as used herein a chimeric gene comprises a coding sequence operably linked to a transcription initiation region that is heterologous to the coding sequence.

The transgenic plants, plant cells, and bacterial cells provided herein express an endolysin or other membrane-disrupting enzyme, in order to reduce the bacterial load on tobacco plants and/or in tobacco products. A number of promoters can be used in the various expression constructs provided herein and each can be selected based on the desired outcome. It is recognized that different applications can be enhanced by the use of different promoters in the recombinant expression constructs to modulate the timing, location and/or level of expression of the endolysin or other membrane-disrupting enzyme. Such recombinant expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

The expression constructs provided herein can be combined with constitutive, tissue-preferred, developmentally-preferred or other promoters for expression in plants. In particular embodiments the promoter can be constitutive and tissue-preferred such that the endolysin is constitutively expressed in a tissue-preferred manner. Likewise, the promoter can be inducible and tissue-preferred. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression cassettes comprise a tissue-preferred promoter. A "tissue preferred" promoter is a promoter that initiates transcription mostly, but not necessarily entirely or solely in certain tissues. For example, nucleic acid molecules encoding endolysins or other membrane-disrupting enzymes can be operably linked to leaf-preferred or stem-preferred promoters.

In some embodiments, the expression construct comprises a cell type specific promoter. A "cell type specific" promoter is a promoter that primarily drives expression in certain cell types in one or more organs, for example, vascular cells in roots, leaves, stalk cells, and stem cells. The expression construct can also include cell type preferred promoters. A "cell type preferred" promoter is a promoter that primarily drives expression mostly, but not necessarily entirely or solely in certain cell types in one or more organs, for example, vascular cells in roots, leaves, stalk cells, and stem cells. The expression constructs described herein can also comprise seed-preferred promoters. In some embodiments, the seed-preferred promoters have expression in embryo sac, early embryo, early endosperm, aleurone, and/or basal endosperm transfer cell layer (BETL). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures for each of these are incorporated herein by reference in their entirety.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of an expression construct within a particular plant tissue. Tissue-preferred promoters are known in the art. See, for example, Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters and stem-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roM promoter (Capana et al. (1994) *Plant Mot Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324).

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256) and maize chlorotic mottle virus leader (MCMV) (Lommel, et al., (1991) *Virology* 81:382-385), herein incorporated by reference in their entirety. See, also, Della-Cioppa, et al., (1987) *Plant Physiology* 84:965-968, herein incorporated by reference in its entirety. Methods known to enhance mRNA stability can also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize Adh1 intron (Kyozuka, et al., (1991) *Mol. Gen. Genet.* 228:40-48; Kyozuka, et al., (1990) *Maydica* 35:353-357) and the like, herein incorporated by reference in their entirety.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in the expression cassettes of the present invention. Examples of suitable reporter genes known in the art can be found in, for example, Jefferson, et al., (1991) in *Plant Molecular Biology Manual*, led. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330, herein incorporated by reference in their entirety.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mot Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518), herein incorporated by reference in their entirety.

Other polynucleotides that could be employed on the expression cassettes disclosed herein include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263: 802), luciferase (Riggs, et al., (1987) *Nucleic Acids Res.* 15(19):8115 and Luehrsen, et al., (1992) *Methods Enzymol.* 216:397-414) and the maize genes encoding for anthocyanin production (Ludwig, et al., (1990) *Science* 247:449), herein incorporated by reference in their entirety.

In still other embodiments, the expression cassette can include an additional polynucleotide encoding an agronomically important trait, such as a plant hormone, plant defense protein, a nutrient transport protein, a biotic association protein, a desirable input trait, a desirable output trait, a stress resistance gene, a disease/pathogen resistance gene, a male sterility, a developmental gene, a regulatory gene, a DNA repair gene, a transcriptional regulatory gene or any other polynucleotide and/or polypeptide of interest. In some embodiments, the expression cassette can include additional polynucleotides that downregulate the expression of genes responsible for agronomically important traits. For example, in some embodiments, the expression cassettes disclosed herein can comprise a nucleic acid sequence that downregulates expression of nicotine.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance. Provided herein are expression cassettes comprising nucleic acid molecules encoding an endolysin or other membrane-disrupting enzyme located on a vector.

Any tobacco species can be modified according to the methods disclosed herein to express an endolysin or other membrane-disrupting enzyme. "Tobacco" or "tobacco plant" refers to any species in the *Nicotiana* genus that produces nicotinic alkaloids. In certain embodiments, tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Pasado, Cubano, Jatim and Bezuki tobaccos), light air cured (e.g., North Wisconsin and Galpao tobaccos), Indian air cured, Red Russian and Rustica tobaccos, as well as various other rare or specialty tobaccos and various blends of any of the foregoing tobaccos. Descriptions of various types of tobaccos, growing practices and harvesting practices are set forth in Tobacco Production, Chemistry and Technology, Davis et al. (Eds.) (1999), which is incorporated herein by reference. Various representative other types of plants from the *Nicotiana* species are set forth in Goodspeed, The Genus *Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Exemplary *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii.*

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO 2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference. Most preferably, the tobacco materials are those that have been appropriately cured and aged. Especially preferred techniques and conditions for curing flue-cured tobacco are set forth in Nestor et al., *Beitrage Tabakforsch. Int.*, 20 (2003) 467-475 and U.S. Pat. No. 6,895,974 to Peele, which are incorporated herein by reference. Representative techniques and conditions for air curing tobacco are set forth in deRoton, C. et al. *Beitrage Tabakforsch. Int.*, 2005, 21, 6, 305-320 and Staaf, M. et al. *Beitrage Tabakforsch. Int.* 2005, 21, 6, 321-330, which are incorporated herein by reference. Certain types of unusual or rare tobaccos can be sun cured. Manners and methods for improving the smoking quality of Oriental tobaccos are set forth in U.S. Pat. No. 7,025,066 to Lawson et al., which is incorporated herein by reference. Representative Oriental tobaccos include katerini, prelip, komotini, xanthi and yambol tobaccos. Tobacco compositions including dark air cured tobacco are set forth in US Patent Appl. Pub. No. 2008/0245377 to Marshall et al., which is incorporated herein by reference. See also, types of tobacco as set forth, for example, in US Patent Appl. Pub. No. 2011/0247640 to Beeson et al., which is incorporated herein by reference. Expression of an endolysin from tobacco plants can reduce the bacterial load on the tobacco plant and in any tobacco product produced from the endolysin-expressing tobacco plant.

As used herein the term plant includes whole plants, plant parts, such as plant organs (e.g. leaves, stems, roots, etc.), seeds, differentiated or undifferentiated plant cells, and progeny of the same. Plant material includes without limitation seeds, suspension cultures, embryos, meristematic regions, callus tissues, leaves, roots, shoots, stems, fruit, gametophytes, sporophytes, pollen, and microspores.

The modified tobacco plants disclosed herein expressing an endolysin or other membrane-disrupting enzyme can be harvested and processed into a tobacco product. As used herein a tobacco product includes leaf tobacco, shredded tobacco, cut tobacco, ground tobacco, powder tobacco, tobacco extract, nicotine extract, smokeless tobacco, moist or dry snuff, kretek, pipe tobacco, cigar tobacco, cigarillo tobacco, cigarette tobacco, chewing tobacco, bidis, bits, cigarette, cigarillo, a non-ventilated recess filter cigarette, a vented recess filter cigarette, a cigar, and tobacco-containing gum, lozenges, patches, electronic cigarettes, or any combination thereof. In certain embodiments, tobacco products provided herein comprise a decreased bacterial load compared to corresponding tobacco products produced by tobacco plants or plant parts not modified to express an endolysin or other membrane-disrupting enzyme.

A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the endolysin described herein); (c) a plant or plant cell which is a non-transformed segregant among progeny of a subject plant or plant cell; or (d) the subject plant or plant cell itself, under conditions in which heterologous nucleic acids encoding an endolysin are not expressed. Similarly, a "control tobacco product" can refer to a tobacco product produced with tobacco plants or plant parts not expressing endolysin, or a tobacco product produced with tobacco in the absence of bacteria modified to express endolysin.

A "control bacteria" or "control bacterial cell" provides a reference point for measuring changes in phenotype of the recombinant bacterial cells. A control bacteria may comprise, for example: (a) a wild-type bacterium, i.e., of the same genotype as the starting material for the genetic alteration which resulted in the subject bacterium; or (b) a bacterium of the same genotype as the starting material but which has been transformed with a null construct (i.e. with a construct which has no known effect on the trait of interest, such as a construct comprising a marker gene).

Any bacterial strain can be modified to express an endolysin. Most bacteria can be classified as Gram-positive (classified principally in the phylum "Actinobacteria") or Gram-negative (classified principally in the phylum "Proteobacteria"). "Gram-negative" as referred to herein relates to bacteria bounded by a cytoplasmic membrane as well as an outer cell membrane, containing only a thin layer of peptidoglycan between the two membranes, which is unable to retain crystal violet stain in a Gram staining technique (whereas Gram-positive bacteria are bounded by only a single unit lipid membrane and contain a thick layer (20-80 nm) of peptidoglycan, which retains the stain).

Exemplary Gram-negative bacteria include, but are not limited to, proteobacteria (e.g., from the genera Enterobacteriaceae (including *Escherichia, Salmonella, Shigella, Serratia, Pantoea, Proteus*, and *Klebsiella*), Pseudomonaceae (including *Pseudomonas* and *Rhizobacter*), Moraxellacae (e.g., *Moraxella* and *Acinetobacter*), Helicobacteracae (e.g., *Helicobacter*), Xanthomonadacae (e.g., *Stenotrophomonas* and *Xanthomonas*), Bdellovibrionacaea (e.g., *Bdellovibrio*), Burkholderiaceae (e.g., *Burkholderia*), Legionellaceae (e.g., *Legionella*), Rhizobiaceae (e.g., *Agrobacterium*); Acetobacteraceae (e.g., acetic acid bacteria), Spirillaceae (e.g., *Spirillum*), and Campylobacteraceae (e.g., *Campylobacter*)).

Gram-positive bacteria include, but not limited to those of the genus, *Bacillus, Clostridium, Enterococcus, Geobacillus, Lactobacillus, Lactococcus, Oceanobacillus, Staphylococcus, Streptococcus*, and *Streptomyces*. For example, the bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells. The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells. In certain embodiments, the bacteria are lactic acid bacteria. As used herein, "lactic acid bacteria" is intended bacteria from a genera selected from the following: *Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus*, and *Weissella* (Holzapfel et al. (2001) *Am. J. Clin. Nutr.* 73:365S-373S; Sneath, ed. (1986) *Bergey's Manual of Systematic Bacteriology* Vol 2, Lippincott, Williams and Wilkins, Hagerstown, MD). In some embodiments, a *Lactobacillus* bacterium is used for expression of the endolysin or other membrane-disrupting enzyme.

In particular embodiments, the bacteria modified to express an endolysin do not substantially facilitate the conversion of nitrate to nitrite (i.e., have little to no affinity for nitrates). Likewise bacteria modified to express an endolysin can act as "nitrite sinks;" and/or have a nitrite reductase gene. As used herein, a nitrite sink is a bacterium that can use nitrite as a terminal electron acceptor. Accordingly, in certain embodiments, microorganisms particularly useful according to the present disclosure for expression of endolysins or other membrane-disrupting enzymes provide for a decreased nitrite concentration in the fermented material as compared to an appropriate control. Bacteria modified to express endolysins can be native bacteria to the tobacco material or non-native bacteria to the tobacco material. Bacteria comprising a nucleic acid sequence or expression cassette as disclosed herein for the expression of endolysin can secrete the endolysin. In such embodiments, the nucleic acid sequence encoding the endolysin or other membrane-disrupting enzyme can further encode a secretion signal or membrane targeting domain to ensure the enzyme is secreted from the bacterial cell or presented of the surface of the bacterial cell. In specific embodiments, the bacterium modified to express an endolysin is resistant to the expressed endolysin such that the bacteria can survive and continue expressing endolysin when the expressed endolysin is present in the bacterial environment.

Methods are provided for the expression of endolysins or other membrane-disrupting enzymes in tobacco plants, plant parts, and plant cells by introducing a nucleic acid molecule comprising a nucleic acid sequence encoding the endolysin or other membrane-disrupting enzyme. The terms "introducing" and "introduced" are intended to mean providing a nucleic acid (e.g., a recombinant expression construct) or protein into a cell. The term "introduced" includes reference to the incorporation of a nucleic acid into a eukaryotic or prokaryotic cell where the nucleic acid may be incorporated into the genome of the cell, and also includes reference to the transient provision of a nucleic acid or protein to the cell. The term "introduced" further includes reference to stable or transient transformation methods, as well as sexually crossing. Thus, "introduced" in the context of inserting a nucleic acid (e.g., a recombinant expression construct) into a cell, means "transfection" or "transformation" or "transduction" and includes the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed.

"Stable transformation" is intended to mean that the nucleotide construct introduced into a host (i.e., a tobacco plant) integrates into the genome of the plant or bacteria and is capable of being inherited by the progeny thereof. "Transient transformation" is intended to mean that a polynucleotide is introduced into the host (i.e., a plant) and expressed temporally.

Transformation protocols as well as protocols for introducing polynucleotide sequences into plants i.e. are well established. Suitable methods of introducing polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981, 840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the recombinant expression constructs disclosed herein can be provided to a tobacco plant using a variety of transient transformation methods. Such transient transformation methods include, but are not limited to, the introduction of the recombinant expression constructs directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, recombinant expression constructs disclosed herein may be introduced into tobacco plants by contacting the tobacco plants or plant parts with a virus or viral nucleic acids. Generally, such methods involve incorporating a nucleotide construct provided herein within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the genome of a tobacco plant or plant part. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the recombinant expression constructs comprising a nucleic acid sequence encoding an endolysin can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The recombinant expression construct is thereby integrated at a specific chromosomal position in the plant genome.

Any method can be used to introduce the nucleic acid molecules and expression cassettes disclosed herein into a plant or plant cell for expression of an endolysin or other membrane-disrupting protein. For example, precise genome-editing technologies can be used to introduce the expression cassettes disclosed herein into the plant genome. In this manner, a nucleic acid sequence will be inserted proximal to a native plant sequence through the use of methods available in the art. Such methods include, but are not limited to, meganucleases designed against the plant genomic sequence of interest (D'Halluin et al (2013) *Plant Biotechnol J* 11: 933-941); CRISPR-Cas9, TALENs, and other technologies for precise editing of genomes (Feng, et al. *Cell Research* 23:1229-1232, 2013, Podevin, et al. *Trends Biotechnology* 31: 375-383, 2013, Wei et al. 2013 *J Gen Genomics* 40: 281-289, Zhang et al 2013, WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb 1-mediated integration (Yau et al. *Plant J* (2011) 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta, H. (2002) *Plant Mol Biol* 48:173-182).

The tobacco plant cells that have been transformed may be grown into plants in accordance with conventional methods. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic (i.e., endolysin expression) identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a recombinant expression construct disclosed herein, stably incorporated into their genome is provided.

Tobacco plant cells that have been transformed to have a recombinant expression construct provided herein can be grown into whole plants. The regeneration, development, and cultivation of plants from single plant protoplast transformants or from various transformed explants is well known in the art. See, for example, McCormick et al. (1986) *Plant Cell Reports* 5:81-84; Weissbach and Weissbach, In: *Methods for Plant Molecular Biology*, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a recombinant miRNA expression construct, stably incorporated into their genome.

In specific embodiments, a nucleic acid molecule comprising a nucleotide sequence encoding an endolysin as described herein can be introduced into a *Nicotiana* plant, plant part, or plant cell. Subsequently, a *Nicotiana* plant or plant part having the introduced inhibitory polynucleotide sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of endolysin polypeptides described herein expressed by the plant. Plant forming conditions are well known in the art and discussed briefly elsewhere herein.

According to the present invention, a control plant or plant part may comprise a wild-type *Nicotiana* plant or plant part, i.e., of the same genotype as the starting material for the genetic alteration that resulted in the subject plant or plant part. A control plant or plant part may also comprise a *Nicotiana* plant or plant part of the same genotype as the starting material but that has been transformed with a null construct (i.e., with a construct that has no known effect on the trait of interest, such as a construct comprising a selectable marker gene). Finally, a control plant or plant part may comprise the subject plant or plant part itself under conditions in which the endolysin sequence is not expressed. In all such cases, the subject plant or plant part and the control plant or plant part are cultured and harvested using the same protocols.

Transformed cells may be grown into *Nicotiana* plants in accordance with conventional methods. See, for example, methods disclosed in Vasil and Hildebrandt (1965) *Science* 150:889; Negaard and Hoffman (1989) *Biotechniques* 7(8): 808-812. These plants may then be grown, and either pollinated with the same transformed line or different lines, and the resulting progeny having expression of the desired phenotypic characteristic identified, i.e., endolysin expression, and thus reduced bacterial load. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein encoding an endolysin or other membrane-disrupting enzyme, for example, an expression cassette of the invention, stably incorporated into their genome.

The transgenic plants of the genus *Nicotiana* as described herein are suitable for conventional growing and harvesting techniques, such as cultivation in manure rich soil or without manure, bagging the flowers or no bagging, or topping or no topping. The harvested leaves and stems may be used in any traditional tobacco product including, but not limited to, pipe, cigar and cigarette tobacco, and chewing tobacco in any form including leaf tobacco, shredded tobacco, or cut tobacco.

For the production of modified bacteria useful as tobacco treatments or inoculants, any method can be used to introduce the nucleic acid molecules and expression cassettes disclosed herein into a bacterial cell for expression of an endolysin or other membrane-disrupting protein. For example, the introduction of DNA into a Gram positive cell may be effected by protoplast transformation (see, e.g., Chang and Cohen, 1979, *Mol. Gen. Genet.* 168: 11 1-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by natural competence (see, e.g., Perry and Kuramitsu, 1981, *Infect. Immun.* 32: 1295-1297), by electroporation (see, e.g., Shigekawa and Dower, 1988, *Biotechniques* 6: 742-751), by transduction (see, e.g., Burke et al., 2001, *Proc. Natl. Acad. Sci. USA* 98: 6289-6294), or by conjugation (see, e.g., Koehler and Thome, 1987, *J. Bacteriol.* 169: 5271-5278). The introduction of DNA into Gram negative cell, such as an *E. coli* cell, may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). However, any method known in the art for introducing DNA into a bacterial host cell can be used. Following introduction of the nucleic acid molecules or expression cassettes disclosed herein into a bacterial cell, the bacterial cell can be cultivated and prepared for application according to standard protocols known in the art and disclosed herein. For example, bacterial cells described herein can be cultured in suitable media, as described generally in Sambrook et al. (1989) *Molecular Cloning, A Laboratory Manual* (2d ed., Cold Spring Harbor Laboratory Press, Cold Spring Harbor, New York).

Bacteria modified to express an endolysin or other membrane-disrupting enzyme can be formulated as a treatment solution or inoculant with a carrier or stabilizer in order to preserve the viability of the bacterial strain and expression of the endolysin. The carrier or stabilizer can be man-made or natural, according to the requirements for application to tobacco products. Such a solution or inoculant can comprise bacteria modified to express an endolysin or other membrane-disrupting enzyme in a concentration of at least $1\times10^6$ CFU/ml, at least $1\times10^8$ CFU/ml, at least $1\times10^{10}$ CFU/ml, at least $1\times10^{11}$ CFU/ml, at least $1\times10^{12}$ CFU/ml, at least $1\times10^{14}$ CFU/ml, at least $1\times10^{15}$ CFU/ml, at least $1\times10^{16}$ CFU/ml, or in a range of $1\times10^6$ CFU/ml to $1\times10^{14}$ CFU/ml, $1\times10^8$ CFU/ml to $1\times10^{14}$ CFU/ml, $1\times10^{10}$ CFU/ml to $1\times10^{14}$ CFU/ml, or $1\times10^{10}$ CFU/ml to $1\times10^{16}$ CFU/ml. The bacterial solution can be a liquid solution, a powder, a gel, or any other form that preserves the viability of the bacteria and/or expression of the endolysin or other membrane-disrupting enzyme.

Expression of the endolysin or other membrane-disrupting enzyme disclosed herein or application of a bacterial inoculant or treatment solution expressing an endolysin or other membrane-disrupting enzyme can reduce the bacterial load on a tobacco plant or plant part (i.e., leaves or stem) or in the final tobacco product. As used herein, the term "a reduced load," "a reduced bacterial load," "reduced microbial load," or reduced "bacterial level" is intended to refer to an reduction in the total amount of bacteria and/or fungi in a treated or transgenic plant of the genus *Nicotiana* or a plant part or tobacco product thereof that is less than what would be found in a plant of the genus *Nicotiana* or a plant part or tobacco product from the same variety of tobacco, processed (i.e., cultured and harvested) in the same manner, that has not been treated or was not made transgenic for expression of endolysin or other membrane-disrupting enzyme. The amount of bacterial load or bacterial level may be reduced by about 10% to greater than about 90%, including greater than about 20%, about 30%, about 40%, about 50%, about 60%, about 70%, and about 80% compared to a control bacterial level. As used herein a "control bacterial level" refers to the total bacterial content on a tobacco plant, plant part, or plant cell not expressing an endolysin. Similarly, a "control bacterial level" refers to the total bacterial content in a tobacco composition, or in a tobacco product produced at least partially with tobacco not expressing an endolysin or another membrane-disrupting enzyme or produced without application of a solution of bacteria expressing endolysin or another membrane-disrupting enzyme. The bacteria load can be measured by any method used in the art for measuring total bacterial content. For example, total bacterial load can be determined by counting the culturable organisms using standard culturing techniques, by determining the population size using PCR or other DNA analysis method, or by DGGE.

A total bacteria count can be conducted using any method known in the art, e.g., by diluting a sample and plating the diluted sample(s) on a growth medium (e.g., plate count agar, PCA). The plate is then incubated, and each bacterium present in the sample is expected to grow into an individual colony on the plate. The resulting colonies can be viewed (e.g., under a microscope) and counted to provide a total bacterial count in colony forming units/gram (CFU/g). Other methods include, but are not limited to, using counting chambers, using membrane filters that are capable of retaining bacteria, photometry and/or spectroscopy (e.g., turbidimetric analysis). The reduction in the total bacteria count in a tobacco plant or plant part expressing endolysin compared to a control tobacco plant can be, for example, a reduction of greater than about 80%, greater than about 85%, greater than about 90%, greater than about 92%, greater than about 95%, or greater than about 96%, based on total bacterial counts (obtained, e.g., by taking colony forming units/gram of a treated tobacco sample, dividing it by colony forming units/gram of an untreated tobacco sample, subtracting the resulting number from 1, and multiplying by 100).

Reducing the bacterial load can include a reduction in the total number or activity of nitrate-reducing bacteria. As used herein, nitrate-reducing bacteria facilitate conversion of nitrate to nitrite. In certain embodiments, reducing the bacterial load comprises a reduction in the nitrate-reducing bacteria that are native to the tobacco. It is recognized that the conversion of nitrates to nitrites, facilitated by such bacteria during fermentation of tobacco, generates precursors that can lead to the formation of certain TSNAs in fermented tobacco material. According to the present disclosure, this conversion of nitrates to nitrites is advantageously minimized (e.g., partially or wholly eliminated) during the fermentation process by the expression of one or more endolysin or other membrane-disrupting enzyme. Reduction of the bacterial load can comprise a reduction of the total Gram-positive bacteria, Gram-negative bacteria, or both Gram-positive and Gram-negative bacteria. "Bacteria" is generally understood to refer to a genus of prokaryotic microorganisms scientifically classified as such. Most bacteria can be classified as Gram-positive (classified principally in the phylum "Actinobacteria") or Gram-negative (classified principally in the phylum "Proteobacteria"). "Gram-negative" as referred to herein relates to bacteria bounded by a cytoplasmic membrane as well as an outer cell membrane, containing only a thin layer of peptidoglycan between the two membranes, which is unable to retain crystal violet stain in a Gram staining technique (whereas Gram-positive bacteria are bounded by only a single unit lipid membrane and contain a thick layer (20-80 nm) of peptidoglycan, which retains the stain).

Expression of an endolysin by a tobacco plant or plant part as disclosed herein can be specific or preferred for Gram-negative bacteria, such as those of bacterial groups, families, genera or species comprising strains pathogenic for humans or animals including Enterobacteriaceae (*Escherichia*, especially *E. coli, Salmonella, Shigella, Citrobacter, Edwardsiella, Enterobacter, Hafiiia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella, Spirochaetaceae* (*Treponema* and *Borrelia*), *Leptospiraceae, Campylobacter, Helicobacter, Spirillum, Streptobacillus, Bacteroidaceae* (*Bacteroides, Fusobacterium, Prevotella, Porphyromonas*), *Acinetobacter*, especially *A. baumannii*. Endolysins specific for Gram-negative bacteria can be expressed or provided with peptides, detergents, or chelators that can be used to permeabilize the Gram-negative outer membrane. In specific embodiments, the level of *Halomonas, Acinetobacter, Burkholderia, Campylobacter, Klebsiella*, or *Pseudomonas* is reduced or eliminated.

In certain embodiments, the endolysin expressed by a tobacco plant or plant part as disclosed herein can be specific or preferred for Gram-positive bacteria such as Gram-positive bacteria of bacterial groups, families, genera or species comprising strains pathogenic for humans or animals, in particular of the phylum Actinobacteria, in particular of the class Actinobacteridae, in particular of the order Actinomycetales, in particular of the families Actinomycineae: Actinomycetaceae (*Actinomyces, Mobiluncus*), Corynebacterineae: Mycobacteriaceae (*Mycobacterium*), Nocardiaceae, Corynebacteriaceae, Frankineae: Frankiaceae, Micrococcineae: Brevibacteriaceae and Propionibacteriaceae (*Propionibacterium*) and of the order Bifidobacteriales, in particular of the families Bifidobacteriaceae (*Bifidobacterium, Falcivibrio, Gardnerella*) and other subclasses: Acidimicrobidae, Coriobacteridae, Rubrobacteridae, Sphaerobacteridae; and of the phylum Firmicutes, in particular of the class Bacilli, in particular of the order Bacillales, in particular of the families: Bacillaceae (*Bacillus*), Listeriaceae (*Listeria*), Staphylococcaceae (*Staphylococcus, Gemella, Jeotgalicoccus*) and of the order Lactobacillales, in particular of the families: Enterococcaceae (*Enterococcus*), Lactobacillaceae (*Lactobacillus, Pediococcus*), Leuconostocaceae (*Leuconostoc*), Streptococcaceae (*Lactococcus, Streptococcus*) and of the class Clostridia, in particular of the order: Clostridiales (*Clostridium, Peptostreptococcus, Selenomonas*), Halanaerobiales and Thermoanaerobacterales, and of the class Tenericutes/Mollicutes, in particular of the order: Mycoplasmatales (*Mycoplasma, Ureaplasma*), Entomoplasmatales (*Spiroplasma*), Anaeroplasmatales (*Erysipelothrix*), Acholeplasmatales (*Acholeplasma*), Haloplasmatales (*Haloplasma*).

In some embodiments, the species of Gram positive bacteria reduced by endolysin expressed by a tobacco plant is a species of the genus *Bacillus, Staphylococcus, Geobacillus, Tetragenococcus, Corynebacterium, Clostridium, Enterococcus*, or *Lactobacillus*, such as *Bacillus* is a *B. licheniformis, B. pumilus, B. subtilis*, or *S. hominis*. In specific embodiments, endolysins specific for gram positive bacteria include Cpl-1 (phage Cp-1), PAL (phage Dp-1), C1or PlyC (phage C1), PlyGBS (phage NCTC11361), PlyG (gamma phage), PlyPH, MV-L (phage MR11), ClyS, CHAPk (bacteriophage K), and LysGH15 (phage GH15).

Tobacco plants and plant parts (i.e., leaves) expressing endolysins can be harvested and processed into tobacco products having a decreased bacterial load. Tobacco is generally harvested and subjected to curing. Traditional techniques of harvesting tobacco plants can be employed as set forth, for example, in US Pat. Appl. Pub. Nos. 2011/0174323 to Coleman, III et al. and 2012/0192880 to Dube et al., which are incorporated by reference herein. In particular embodiments, harvested tobaccos that are grown, harvested and processed in accordance with the present invention can be subjected to curing processes that can be characterized as providing so-called air cured or dark-fired tobaccos. See, for example, those types of curing processes set forth in Tobacco Production, Chemistry and Technology, Davis et al. (Eds.) (1999); Roton et al., Beitrage Tabakforsch Int., 21, 305-320 (2005); Staaf et al., Beitrage Tabakforsch Int., 21, 321-330 (2005) and U.S. Pat. No. 1,327,692 to Beinhart; U.S. Pat. No. 2,758,603 to Heljo; U.S. Pat. No. 5,676,164 to Martin; U.S. Pat. No. 6,755,200 to Hempfling et al.; U.S. Pat. No. 7,293,564 to Perfetti et al.; U.S. Pat. No. 7,650,892 to Groves et al.; U.S. Pat. No. 8,353,300 to Li et al.; and US Pat. Appl. Pub. Nos. 2010/0116281 and 2012/0279510 to Marshall et al., and 2014/0299136 to Moldoveanu et al., which are all incorporated herein by reference.

In some embodiments, bacteria modified to express endolysin as disclosed herein can be used as treatments by contacting the modified bacteria with unharvested tobacco material up to about 24 hours before harvest. In other treatment embodiments the bacteria is provided in a solution comprising one or more carriers or stabilizers. Contacting unharvested tobacco with bacteria expressing endolysin or other membrane-disrupting enzymes can provide a treated tobacco material having a reduced total bacterial load following harvest. The unharvested tobacco material can be, for example, selected from the group consisting of a tobacco seed, a tobacco seedling, an immature live plant, a mature live plant, or a portion thereof. In certain embodiments, the total bacterial content of the treated tobacco material is reduced by at least about 50% in number following harvest and in certain embodiments, the total bacterial content of the treated tobacco material is reduced by at least about 80% in number following harvest. In some embodiments, the total bacterial content of the tobacco material comprises Gram-negative bacteria and wherein the Gram-negative bacterial content of the treated tobacco material is reduced by at least about 50% in number following harvest.

Tobacco plants or plant parts can further be treated with enzymes prior to harvest or following harvest. Enzymatic treatment of tobacco can have various effects on the resulting tobacco products. For example, certain enzymes are known to promote disease resistance, modify the growth of plants, modify the structure of plant cells, and affect the release and/or reaction of certain compounds within the plants, among other functions. It is noted that the specific results obtained by enzymatic treatment may be related, at least in part, to the specific type of enzyme or enzymes that are used in the treatment. See, U.S. Patent Appl. Publication No. 20170035098, herein incorporated by reference.

The one or more enzymes applied to the tobacco plant or plant part can comprise amylases (which catalyze the breakdown of starch into sugars) or proteases (which catalyze the hydrolysis of peptide bonds of proteins) or a combination thereof. Amylases can include alpha-amylase, beta-amylase, gamma-amylase, or a combination thereof. Proteases can include serine proteases, threonine proteases, cysteine proteases, asparatate proteases, metalloproteases, and glutamic acid proteases and certain exemplary proteases include, but are not limited to, protease *Bacillus licheniformis*, protease *Bacillus* sp., protease *Aspergillus oryzae*, protease *Bacillus amyloliquefaciens*, protease *Bacillus*, and protease *Streptomyces griseus*, which can include commercially available enzyme products ALCALASE™, Esperase™, Everlase™, Flavourzyme™, Neutrase™, Protamex™, Savinase™, and Substilisin A™ from Novozymes A/S In certain embodiments, the one or more enzymes comprise asparaginase (e.g., PreventASe™, DSM Food Specialties, Heerlen, NL and Acrylaway™, Novozymes,A/S, Bagsvaerd, DK). In certain embodiments, the one or more enzymes comprise a polyphenol oxidase (PPO). In some embodiments, the one or more enzymes comprise an oxidase such as a monophenol oxidase enzyme (tyrosinase) or an o-diphenol oxygen oxidoreductase enzyme (catechol oxidase). Another exemplary oxidase for use according to the invention is laccase.

Enzymes used according to the methods disclosed herein can be "GRAS" (Generally Regarded as Safe), although non-GRAS enzymes can be used in certain embodiments. In certain embodiments, the enzyme is an enzyme that is capable of toxicant reduction within the plant or plant component or capable of reduction of a precursor of a toxicant produced during general processing (e.g., heat treatment) or use of the plant or a component thereof.

In certain embodiments, the endolysin and/or enzymatic treatment described herein can be used in combination with probiotic treatment, as described in U.S. patent application Ser. No. 13/444,272 to Marshall et al., filed on Apr. 11, 2012, which is incorporated herein by reference. As disclosed therein, certain exemplary probiotics include, but are not limited to, *Bifidobacterium adolescentis, Bifidobacterium animalis, Bifidobacterium bifidum, Bifidobacterium breve, Bifidobacterium infantis, Bifidobacterium lactis, Bifidobacterium longum, Bifidobacterium pseudocatenulatum, Bifidobacterium pseudolongum, Bifidobacterium sp., Bifidobacterium thermophilum, Lactobacillus acidophilus, Lactobacillus alimentarius, Lactobacillus amylovorus Lactobacillus bulgaricus, Lactobacillus bifidus, Lactobacillus brevis, Lactobacillus casei, Lactobacillus caucasicus, Lactobacillus crispatus, Lactobacillus curvatus, Lactobacillus delbruckii, Lactobacillus fermentum, Lactobacillus gallinarum, Lactobacillus gasseri, Lactobacillus helveticus, Lactobacillus johnsonii, Lactobacillus lactis, Lactobacillus leichmannii, Lactobacillus paracasei, Lactobacillus plantarum, Lactobacillus reuteri, Lactobacillus rhamnosus, Lactobacillus salivarius, Lactobacillus sp., Lactobacillus sporogenes, Lactococcus lactis, Streptococcus cermoris, Streptococcus faceium, Streptococcus infantis, Streptococcus thermophilus, Enterococcus faceium, Pediococcus acidilactici, Staphylococcus thermophilus, Staphylococcus carnosus, Staphylococcus xylosus, Saccharomyces boulardii, Saccharomyces cerevisiae, Saccharomyces boulardii, Bacillus cereus var toyo, Bacillus subtilis, Bacillus coagulans,* and *Bacillus licheniformis*. In further embodiments, the enzyme treatment can be used in combination with treatment with one or more yeasts. Where enzymatic treatment of a tobacco plant or plant component is used in combination with one or more additional types of treatment (e.g., treatment with amino acid, cations, saccharides, reducing agents, phenolic compounds, thiol-containing compounds, oxidizing agents, oxidation catalysts, natural plant extracts, and/or probiotics), the treatments can be performed simultaneously, in close succession, or at significantly different time points. The enzyme and one or more reagents can be incorporated within the same formulation or different formulations. In some embodiments, the enzyme and one or more reagents can be provided in separate formulations and applied at different points of the tobacco plant life cycle (e.g., with one applied to growing plants in the field and one applied following harvest or with one applied to seeds and one applied to growing plants in the field).

In certain embodiments (e.g., where tobacco material is being prepared for use in certain smokeless tobacco products), cured tobacco material is then fermented. Fermentation generally requires subjecting the tobacco material to water (e.g., humidity) and heat. The fermentation process can be conducted in a chamber where the temperature and moisture content can be controlled. As a consequence of the elevated temperature and moisture content to which the tobacco is exposed during the fermentation process, certain components (e.g., ammonia) may be effectively removed from the tobacco. In some embodiments, fermentation is a bacterial process, wherein certain bacteria produce enzymes that react to produce flavor precursors within the fermenting tobacco material. See, e.g., S. Gilliland, Ed., *Bacterial Starter Cultures for Foods*, CRC Press, Inc. (Boca Raton, Fla.), at pg. 97-118, which is incorporated herein by reference. In some embodiments, the bacterial load of fermented tobacco produced from modified tobacco plants expressing an endolysin as disclosed herein is lower than the bacterial load of fermented tobacco produced by wild-type tobacco or tobacco not expressing an endolysin.

In certain embodiments, tobacco is treated and fermented according to the specific process detailed below. A tobacco material is received and can optionally be stored at a given moisture level (e.g., at about 13-18% moisture) for a given period of time, such as at least about a year, e.g., between about 1 and about 3 years. The tobacco material is generally treated with moisture to bring the moisture level of the tobacco material within a given range of moisture (e.g., at least about 15%, at least about 20%, between about 15% and about 30%, or between about 20% and about 25%, such as about 22% moisture in one embodiment) at a given temperature (e.g., at a temperature of about 100° F. or greater, a temperature of about 110° F. or greater, a temperature of about 120° F. or greater, or a temperature of about 130° F. or greater, such as within the range of about 120° F. to about 150° F., or about 130° F. to about 150° F., such as about 140° F. in one embodiment). It is noted that particularly beneficial values can depend on the type of tobacco being treated and thus, these values can be adjusted accordingly.

When the fermentation is completed to the desired extent, the fermented tobacco material is typically treated with heat. This heat treatment can, in some embodiments, be sufficient to stop the fermentation and heat kill any active, vegetative microbes. In some embodiments, various components can then be added to the heat treated fermented tobacco material. For example, preservatives, casings, moisture, and salinity can be adjusted through addition of the appropriate components to the heat treated fermented tobacco material (e.g., by adding such components directly to the fermentation vessel). Alternatively, in some embodiments certain components can be added prior to fermentation when it is advantageously to adjust the pool of reagents prior to fermentation. In certain embodiments, following the method disclosed above, the heat treated tobacco material can be dried (e.g., to a moisture level of between about 15% and about 20%, e.g., about 18% moisture) for storage and shipping. Such heat treated tobacco material can be subsequently processed, e.g., by adjusting the final salinity, preservative, casing and moisture content.

Bacterial strains expressing an endolysin or other membrane degrading protein, as disclosed herein, can be applied to tobacco at any point in the processing, fermentation, or production process. In specific embodiments, bacterial strains expressing an endolysin can be applied to a tobacco product as a treatment solution or inoculant prior to fermentation or during fermentation. In specific embodiments, the an effective amount of bacteria modified to express an endolysin or other membrane-disrupting enzyme can be added to tobacco within 24 hours of curing, within 12 hours of curing, within 8 hours of curing, within 6 hours of curing, within 4 hours of curing, or within 2 hours of curing. In certain embodiments an effective amount of bacteria modified to express an endolysin or other membrane-disrupting enzyme can be added to tobacco during the curing process.

In accordance with the present disclosure, an effective amount of bacteria expressing endolysin is used as a treatment of a tobacco plant or plant part, or a tobacco composition, in order to reduce the bacterial load in a tobacco product produced from the plant, plant part, or tobacco composition. An "effective" amount is any amount of the bacterium expressing an endolysin or other membrane-disrupting enzyme, that when applied to a tobacco plant or plant product, or to a tobacco composition, is sufficient for a measurable reduction in bacterial load of the treated tobacco composition as compared to a control, as described herein. For example, in some embodiments, bacterial cells can be added in a concentration of at least $1 \times 10^6$ CFU/g, at least $1 \times 10^8$ CFU/g, at least $1 \times 10^{10}$ CFU/g, at least $1 \times 10^{11}$ CFU/g, at least $1 \times 10^{12}$ CFU/g, at least $1 \times 10^{14}$ CFU/g, at least $1 \times 10^{15}$ CFU/g, at least $1 \times 10^{16}$ CFU/g, or in a range of $1 \times 10^6$ CFU/g to $1 \times 10^{14}$ CFU/g, $1 \times 10^8$ CFU/g to $1 \times 10^{14}$ CFU/g, $1 \times 10^{10}$ CFU/g to $1 \times 10^{14}$ CFU/g, or $1 \times 10^{10}$ CFU/g to $1 \times 10^{16}$ CFU/g.

The method of application of the bacterial treatment solution as disclosed herein will often depend, at least in part, on the stage of the tobacco plant. For example, in certain embodiments, a solution comprising bacteria expressing an endolysin or other membrane degrading protein, as disclosed herein are applied to a tobacco seed prior to planting. In such embodiments, the treatment solution can be applied in the form of a seed treatment or coating. For example, the seeds can be dipped in such a solution, soaked in the solution, or sprayed with the solution. In certain embodiments, the bacterial solution can be applied to a tobacco in seedling or unharvested (live) plant form or may be applied to the soil in which the tobacco plants will be planted or are presently planted. In such embodiments, spray application of the bacterial solution can be used (e.g., using a hydraulic boom sprayer, air blast sprayer, sprinkler system, fogger, or aerial sprayer), although the method of application is not limited thereto. Certain methods to treat plants with microorganisms which could be used, or readily modified for suitable use, in the present invention are provided in U.S. Pat. No. 4,140,136 to Geiss et al.; U.S. Pat. No. 4,151,848 to Newton et al.; U.S. Pat. No. 4,308,877 to Mattina et al.; U.S. Pat. No. 4,476,881 to Gravely et al.; U.S. Pat. No. 4,556,073 to Gravely et al.; U.S. Pat. No. 4,557,280 to Gravely et al.; U.S. Pat. No. 4,566,469 to Semp et al.; U.S. Pat. No. 5,372,149 to Roth et al.; U.S. Pat. No. 7,549,425 to Koga et al.; U.S. Pat. No. 7,549,426 to Koga et al.; and U.S. Pat. No. 7,556,046 to Koga et al., all of which are incorporated herein by reference. Although it may be advantageous to apply the bacterial treatment solution (i.e., bacteria expressing endolysin or other membrane-disrupting enzyme) while the tobacco plant is still in living form, it is also possible in some embodiments to apply the treatment solution following harvesting of the tobacco plants. Such application can occur at any time following harvest, including immediately following harvest, prior to or following post-harvest processing (e.g., drying, curing, and/or physical processing of the plant), or at any stage in between. Advantageously, the treatment is conducted prior to any significant curing of the tobacco plant material. The application of bacterial treatment solution can be done at one stage in the plant life cycle, or can be conducted at two or more stages.

The tobacco material comprising reduced bacterial levels (resulting from expression of endolysin in tobacco, as disclosed herein, or application of bacteria expressing an endolysin to a tobacco plant or plant part, or to a tobacco composition, as disclosed herein) can lead to modified levels of other types of compounds in the tobacco material after curing as compared with untreated tobacco material after curing. Such compounds may, in certain embodiments, be smoke toxicants and/or smoke toxicant precursors. For example, it is believed that certain compounds are produced, at least in part, by the action of bacteria (e.g., gram negative bacteria) during the curing process. Specifically, bacteria can produce the enzyme nitrate reductase, which converts nitrates to nitrite and nitric oxide; nitric oxide can subsequently react with precursor tobacco alkaloids to produce tobacco-specific nitrosamines (TSNAs). Exemplary TSNA compounds include N-nitrosonornicotine (NNN), 4-methyl-N-nitrosamino-1-(3-pyridyl)-1-butanone (NNK), N-nitrosoanatabine (NAT), 4-methyl-N-nitrosamino-1-(3-pyridyl)-1-butanol (NNAL), and N-nitrosoanabasine (NAB).

Although low levels of TSNA are typically observed in green tobacco material, it is generally understood that TSNAs are formed during tobacco curing, fermentation, and/or aging processes. Consequently, various efforts to reduce TSNA levels by modifying the growth or curing process have been attempted. See, for example, U.S. Pat. Nos. 4,343,317 and 4,347,859 to Bokelman; U.S. Pat. No. 5,803,081 to O'Donnell; U.S. Pat. No. 6,202,649 to Williams; U.S. Pat. No. 6,805,134 to Peele; U.S. Pat. No. 7,293,564 to Perfetti et al.; U.S. Pat. No. 7,404,406 to Peele; U.S. Pat. No. 8,353,300 to Li et al.; US Pat. Appl. Publ. No. 2012/0234334 to Chen et al.; PCT Appl. Publ. Nos. WO 83/01180 to Malik; WO 98/05226 and WO 98/58555 to Williams; and WO 01/35770 and WO 02/13636 to Hempfling et al., WO 03/094639 to Koga et al., and Muller et al. Molec. Gen. Genet. 1987, 161, 67-76, which are all incorporated herein by reference.

Accordingly, modifying the level of bacteria (e.g., gram negative bacteria) generally associated with tobacco material subjected to curing can, in some embodiments, lead to a cured tobacco material having a modified level of TSNAs (e.g., fewer TSNAs by weight than in a comparable tobacco material that has not been treated prior to curing as described herein). In certain embodiments of the invention, the decrease in the level of TSNAs can vary but generally, a treated, cured tobacco will comprise between about 10% and about 90% by weight of TSNAs generally as compared with the amount of TSNAs present in a comparable cured (but untreated) tobacco. For example, in certain embodiments, treated tobacco material may exhibit at least a 10%, 20%, 30%, 40%, 50%, 60%, 70%, or 80% decrease in TSNA compounds by weight after curing as compared with curing control level of TSNA. As used herein a "control level of TSNA" refers to the TSNA level in a tobacco product produced from tobacco plants not modified to express an endolysin or other membrane-disrupting enzyme. A "control level of TSNA" also refers to the level of TSNA in an existing tobacco product or a standard level of TSNA recognized for an individual tobacco product. Likewise, a "control level of TSNA" can refer to the TSNA level of a tobacco product produced without using a solution of bacteria expressing an endolysin or other membrane-disrupting enzyme. Thus, the TSNA level in a tobacco product can be reduced by producing the tobacco product, at least partially, using tobacco plants or plant parts modified to express endolysin and/or by treating a tobacco with a plant or plant part, or a tobacco composition with a treatment solution comprising bacteria modified to express endolysin or another membrane-disrupting enzyme.

The extent of TSNA reduction that can be achieved by the expression of an endolysin in a tobacco plant or plant part can be significant. In certain embodiments, the total TSNA level of tobacco material produced from tobacco plants expressing endolysin after the tobacco material is cured or produced from a tobacco composition treated with a bacterial solution as disclosed herein is less than about 2,000 ng/g, less than about 1,000 ng/g, less than about 500 ng/g, less than about 250 ng/g, or less than about 200 ng/g. In some embodiments, the total TSNA level of tobacco material produced following the application of bacteria expressing endolysin after the tobacco material is cured is preferably less than about 2,000 ng/g, less than about 1,000 ng/g, less than about 500 ng/g, less than about 250 ng/g, or less than about 200 ng/g.

Exemplary fermentation processes for tobacco are provided in U.S. Pat. No. 2,927,188 to Brenik et al.; U.S. Pat. No. 4,660,577 to Sensabaugh et al.; U.S. Pat. No. 4,528,993 to Sensabaugh et al.; and U.S. Pat. No. 5,327,149 to Roth et al., which are incorporated herein by reference. Fermentation is understood to be enhanced by the presence of, e.g., *Lactobacillus*; consequently, modification of the amount of *Lactobacillus* bacteria associated with a given sample (e.g., by means of a lactic acid bacteria treatment solution as disclosed above) can, in some embodiments, impact the fermentation of that sample. Where that treated tobacco is later subjected to fermentation, the fermentation can, in some embodiments, be enhanced by the presence of a greater number of *Lactobacillus* bacteria. In some embodiments, the *Lactobacillus* bacterium expresses an endolysin or other membrane-disrupting enzyme. By "enhanced" is meant that the fermentation process proceeds, for example, more quickly, and/or more uniformly.

In certain embodiments of the present disclosure, the bacteria type and/or count on the tobacco during fermentation can be further modified by treating the tobacco with one or more microorganisms (e.g., bacteria, yeast, fungi, etc.) expressing endolysin just prior to or during fermentation. When the fermentation is completed to the desired extent, the fermented tobacco material is typically treated with heat. This heat treatment can, in some embodiments, be sufficient to stop the fermentation and heat kill any active, vegetative microbes. This post-fermentation heat treatment can be achieved, for example, in a manner similar to that described above with respect to heat treatment prior to fermentation. In some embodiments, various components can then be added to the heat treated fermented tobacco material. For example, preservatives, casings, moisture, and salinity can be adjusted through addition of the appropriate components to the heat treated fermented tobacco material (e.g., by adding such components directly to the fermentation vessel). Alternatively, in some embodiments certain components can be added prior to fermentation when it is advantageously to adjust the pool of reagents prior to fermentation. In certain embodiments, following the method disclosed above, the heat treated tobacco material is dried (e.g., to a moisture level of between about 15% and about 20%, e.g., about 18% moisture) for storage and shipping. Such heat treated tobacco material can be subsequently processed, e.g., by adjusting the final salinity, preservative, casing and moisture content.

After treatment, the treated tobacco material can be used in a green form (e.g., the plant or portion thereof can be used without being subjected to any curing process). For example, the plant or portion thereof can be used without being subjected to significant storage, handling or processing conditions. In certain situations, it is advantageous for the plant or portion thereof be used virtually immediately after harvest. Alternatively, for example, a plant or portion thereof in green form can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use. It is understood that the benefits, e.g., reduced TSNA formation, enhanced fermentation, and the like, are realized after curing; therefore, the treated materials described herein are advantageously cured prior to use, e.g., in a tobacco product.

Tobacco compositions intended to be used in a smokable or smokeless form may incorporate a single type of tobacco (e.g., in a so-called "straight grade" form). For example, the tobacco within a tobacco composition may be composed solely of flue-cured tobacco (e.g., all of the tobacco may be composed, or derived from, either flue-cured tobacco lamina or a mixture of flue-cured tobacco lamina and flue-cured tobacco stem. The tobacco within a tobacco composition also may have a so-called "blended" form. For example, the tobacco within a tobacco composition of the present invention may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other exemplary tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other exemplary tobacco blends incorporate about 20 to about 30 parts Oriental tobacco and about 70 to about 80 parts flue-cured tobacco.

Tobacco compositions, as described herein, can be treated or inoculated with a solution of modified bacterium expressing an endolysin or other membrane-disrupting enzyme. Such treatment or inoculation can occur prior to or during the curing process. Likewise, treatment of a tobacco composition with a modified bacterium expressing an endolysin or other membrane-disrupting enzyme can occur prior to or during fermentation of the tobacco. Accordingly, a "control tobacco composition" refers to a tobacco composition that has not been treated or inoculated with a modified bacterium expressing an endolysin or other membrane-disrupting enzyme. Thus, in order to identify a decrease in bacterial load of a tobacco composition having been treated with a solution of modified bacteria expressing an endolysin or other membrane-disrupting enzyme, the bacterial load of the treated tobacco composition can be compared to that of a control tobacco composition.

The tobacco materials provided according to the present disclosure can be further processed and used in ways generally known in the art. See, for example, U.S. Patent Appl. Publ. Nos. 2012/0272976 to Byrd et al. and 2014/0299136 to Moldoveanu et al., which are incorporated herein by reference. In various embodiments, the tobacco can be employed in smoking articles, smokeless tobacco products, and electronic smoking articles. Certain tobacco materials described herein can find use, for example, in products wherein decreased bacterial load is advantageous to the final tobacco product.

Of particular interest are smokeless tobacco products comprising tobacco materials treated as described herein, the makeup of which can vary. See, for example, those representative components, combination of components, relative amounts of those components and ingredients relative to tobacco, and manners and methods for employing those components, set forth in U.S. Pat. No. 8,061,362 to Mua et al. and U.S. Pat. Pub. Nos. 2007/0062549 to Holton, Jr. et al.; 2007/0186941 to Holton, Jr. et al.; and 2008/0029110 to Dube et al., each of which is incorporated herein by reference.

In certain embodiments, snus or snuff-type products (e.g., ground tobacco materials incorporated within sealed pouches) produced from the modified tobacco plants or plant parts disclosed herein, e.g., including, tobacco plants expressing endolysins (alone or in combination with other types of tobacco materials) are provided. Likewise, snus or snuff-type products produced from tobacco material treated with bacteria expressing endolysin or other membrane-disrupting enzymes are provided. Exemplary embodiments of such snus products are illustrated and described, for example, in US Pat. App. Publ. No. 20120279510 to Marshall et al., which is incorporated herein by reference. Descriptions of various components of snus products and components thereof also are set forth in U.S. Pat. Pub. No. 2004/0118422 to Lundin et al., which is incorporated herein by reference. See, also, for example, U.S. Pat. No. 4,607,479 to Linden; U.S. Pat. No. 4,631,899 to Nielsen; U.S. Pat. No. 5,346,734 to Wydick et al.; and U.S. Pat. No. 6,162,516 to Derr; and U.S. Pat. Pub. Nos. 2005/0061339 to Hansson et al. and 2010/0018539 to Brinkley et al., each of which is incorporated herein by reference.

The relative amount of tobacco material (e.g., a milled tobacco material or an aqueous tobacco extract) within the smokeless tobacco composition may vary, but tobacco material is typically the predominate ingredient. Preferably, the amount of tobacco material formulation within the smokeless tobacco composition is at least about 25 percent or at least about 30 percent, on a dry weight basis of the tobacco composition. In certain instances, the amounts of other components within the smokeless tobacco composition may exceed about 40 percent, on a dry weight basis. A typical range of tobacco material formulation within the smokeless tobacco composition is about 25 to about 60 dry weight percent, more typically about 30 to about 40 dry weight percent.

The smokeless tobacco composition can be provided in any suitable predetermined shape or form, and most preferably is provided as a molded product (e.g., formed in the general shape of a pill, pellet, tablet, sheet, coin, bead, ovoid, obloid, cylinder, bean, stick, rod, cube, or the like). The mouthfeel of certain embodiments of the smokeless tobacco product can be characterized by a smooth and creamy texture. According to one aspect, the smokeless tobacco product is capable of lasting in the user's mouth without chewing for about 2-3 minutes, meaning the user of the product is formulated for enjoyment in the oral cavity of about 2 to about 3 minutes before swallowing.

Certain smokeless tobacco compositions can incorporate tobacco as the major component thereof. In some embodiments, the tobacco plants or plant parts modified to express endolysin as described herein, or otherwise treated with a bacterium expressing an endolysin as described herein, account for about 10%, 20%, 30%, 40%, 50%, 60%, 70%, 80%, 90%, or 100% of the tobacco in a smokeless tobacco product. In certain embodiments, those products do not, to any substantial degree, leave any residue in the mouth of the user thereof. In addition, certain embodiments of those products do not provide the user's mouth with a slick, waxy or slimy sensation, but instead provide a smooth and creamy sensation when in the mouth of the user.

Products of the present invention may be packaged and stored in any suitable packaging. See, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 7,946,450 to Gelardi et al.; U.S. Pat. No. 8,033,425 to Gelardi; U.S. Pat. No. 8,066,123 to Gelardi; D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0230003 to Thiellier; 2010/0084424 to Gelardi; 2010/0133140 to Bailey et al; 2010/0264157 to Bailey et al.; 2011/0168712 to Gelardi et al.; and 2011/0204074 to Bailey et al., which are incorporated herein by reference.

The following examples are provided to illustrate further aspects associated with the present disclosure, but should not be construed as limiting the scope thereof. Unless otherwise noted, all parts and percentages are by dry weight.

EXPERIMENTAL

Example 1—Transformation of Tobacco with Nucleic Acid Molecule Encoding Endolysin Transgenic plants are generated to investigate the efficiency of endolysin production in tobacco plants; a first using a nucleic acid sequence encoding an endolysin operably linked to a constitutive promoter; a second using a nucleic acid sequence encoding an endolysin operably linked to a leaf-preferred promoter; and a third using a nucleic acid sequence encoding an endolysin operably linked to a stem-preferred promoter. An expression vector, specific for each coding sequence and promoter combination is used, which has, for example, a NOS terminator, as well as a cassette having a selection marker, such as a kanamycin selection marker (NPT II) under direction of a promoter, such as the actin2 promoter, and a terminator, such as a NOS terminator. The nucleic acid constructs carrying the endolysin transgenes of interest are introduced into tobacco leaf discs, for example, using an *Agrobacterium* transformation approach.

For example, tobacco plants (Narrow Leaf Madole (NLM)) are grown from magenta boxes, and leaf disks are cut into 15×150 mm plates. *Agrobacterium tumefaciens* containing the target plasmid are collected by centrifugation of about 20 ml cell suspension in about 50 ml centrifuge tube at about 3500 rpm for about 10 minutes. Supernatant is removed and *Agrobacterium* cell pellet is resuspended, such as in 40 ml liquid resuspension medium. About 25 ml of the solution is transferred to each 15×100 mm Petri plates. In those 15×150 mm plates, tobacco leaves, avoiding the midrib, are cut into about a 0.6 cm disk. Leaf disks are placed upside down, a thin layer of MS/B5 liquid resuspension medium is added, and slices are made with a #15 razor blade. The leaf discs are poked uniformly with a fine point needle. Eight disks are placed, upside down, in each regeneration plate (15×100 mm). *Agrobacterium tumefaciens* suspension is added and the leaf discs are incubated for 10 minutes.

Leaf disks are transferred to co-cultivation plates (½ MS medium) and disks are placed upside down in contact with filter paper overlaid on the co-cultivation TOM medium (MS medium with 20 g sucrose/L; 1 mg/L IAA and 2.5 mg/L BAP). The plate is sealed with parafilm and labeled appropriately. Plates are incubated in dim light (60-80 mE/ms) and 18/6 photoperiods at 24° C. for three days. Leaf disks are transferred to regeneration/selection TOM K medium plates (TOM medium with 300 mg/l Kanamycin) and subculture bi-weekly to the same fresh medium in dim light at 24° C. until shoots become excisable. Shoots from leaves are removed with forceps and inserted in MS basal medium with with about 100 mg/L kanamycin at 24° C. and 18/6 photoperiods with light intensity of 6080 mE/ms for rooting.

When plantlets with both shoots and roots have grown large enough (e.g., reach over half of a GA7 box), they are transferred to soil for acclimatization. During the transfer, the gel is washed from the root tissue with tap water. Established seedlings are transferred to the greenhouse for further analysis and to set seed.

Efficacy testing for endolysin production are conducted following plant growth to produce adequate material for testing.

Example 2. Endolysin Testing

Endolysins isolated from tobacco plants that may be produced essentially as described in Example 1 are tested for antimicrobial activity. For example, *E. coli* DSMZ 11753, *Acinetobacter baumannii* DSMZ 30007, and *Pseudomonas aeruginosa* PAO1p cells are used as test strains. Overnight cultures are diluted about 10-fold in fresh LB medium and grown to $OD_{600}$=0.6. The culture is spun down and diluted 10-fold in dilution buffer (10 mM HEPES, 0.5 mM EDTA; pH 7.4). Bacteria are incubated at room temperature with each 10 µg undialyzed fusion protein at a final concentration of 100 µg/ml in buffer (20 mM $NaH_2PO_4$—NaOH pH 7.4; 0.5 M NaCl; 0.5 M imidazole). After about 1 hour cell dilution series are made in PBS and plated on LB. Additionally, a negative control is plated using buffer (20 mM $NaH_2PO_4$—NaOH pH 7.4; 0.5 M NaCl; 0.5 M imidazole). The residual colonies are counted after an overnight incubation at 37° C. Based on the counted cell numbers, the antibacterial activity as logarithmic units (=$\log_{0.10} N_0/N_i$ with $N_0$=number of untreated cells and $N_i$=number of treated cells) is calculated. All samples are replicated at least in four-fold.

Example 3. Preparation of a Smokeless Tobacco Composition

A smokeless tobacco composition suitable for use as a meltable smokeless tobacco product (STP) for oral use is provided in the following manner using harvested tobacco leaves expressing endolysin. A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided. The lipid substance is a non-hydrogenated lauric coating fat containing a blend of palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold.

Example 4. Reduction of Bacterial Load in Tobacco Product Produced with Tobacco Plant Producing Endolysin Detection of Culturable Bacteria: The viable and culturable bacteria are identified essentially by growth on three different media. Culturing of bacteria is done on the day of initial sampling (day 1) and subsequently on about days 3, 5, 8, and 15. Between samplings, the smokeless tobacco products produced with tobacco expressing endolysin are stored at 25° C. in ambient conditions.

For culturing, about 100-µl aliquots of the tobacco suspension are transferred to: a) SBA, b) mannitol salt agar (MSA), and c) MacConkey agar plates (MAC). For the initial sampling, the plates are incubated at 25, 37, and 42° C. and observed for growth. If there are no distinguishable differences of colonies growing at the different temperatures, the 37° C. incubation temperature is used for subsequent cultures. Visually unique bacterial colonies are selected and described; representative colonies were subcultured, identified (as described below), and archived in BHI broth with 20% glycerol at −80° C. for long term storage.

Bacterial Identification. Bacterial colonies are picked from the subculture plates and added to sterile water in PCR tubes or 96-well plates and thoroughly mixed. The suspensions are heated to about 99° C. for about 10 min to lyse the bacterial cells and liberate the DNA template for amplification and sequencing of the 16S rRNA gene. For the 16S rDNA analyses, the template DNA is combined with 2× PCR Mastermix and common PCR primers are used to amplify a fragment of the 16S rDNA using a PCR protocol with an initial denaturation at 95° C., followed by 40 cycles of 1 min at 94° C., 1 min at 55° C. and 2 min at 72° C. with a final 5 min extension at 72° C. The PCR products are separated by agarose gel electrophoresis to verify the presence of a product, purified by membrane filtration and prepared for DNA sequencing. The amplified products are sent to a core sequencing facility for sequencing. The resultant sequences are visually inspected and submitted to GenBank to identify the bacterial genus and, in most cases, species.

Example 5. Treatment of Tobacco Plants with Solution of Bacteria Expressing Endolysin Dark-air cured tobacco is treated five hours prior to harvest with a solution comprising about $1 \times 10^{12}$ CFU/ml bacteria modified to express endolysin. The solution is applied using a backpack sprayer. Solutions are based on a 100 gallon solution per acre, using recommended plant spacings.

The treated tobacco is harvested and mid-stalk leaf samples are analyzed for total bacteria counts and enteric bacteria counts. Ten grams of each treated tobacco sample is placed in Butterfields Phosphate Buffer and diluted about $10^{-2}$ to $10^{-8}$ times with water. The treated tobacco sample dilutions are applied to plate count agar (PCA) for total aerobic bacteria counts, to violet red bile agar (VRBA) for gram negative bacteria counts, and to MRS for anaerobic (*Lactobacillus*) counts. The number of bacterial colonies, as visualized under magnification, are counted to estimate the total number of colony-forming units per gram, CFU/g.

Example 6. Treatment of Cut Tobacco with Solution of Bacteria Expressing Endolysin Tobacco (e.g., tobacco treated by any of the methods presented above) is subjected to fermentation by moistening the tobacco (e.g., by subjecting the tobacco to humid conditions). Control of endogenous bacteria, yeast, and fungi are controlled during the fermentation process by selecting and maintaining appropriate water activity, pH, salinity, and temperature conditions to provide appropriate conditions for the starter culture or desired endogenous microorganism(s) to ferment the tobacco and prevent TSNA precursor formation. A solution of bacteria modified to express endolysin alone, or in combination with yeast, is applied to the fermenting tobacco and the tobacco is fermented under such conditions for a period of about 1 to 6 weeks.

Example 7. Identification and Specific Bacterial Numbers Present in Smokeless Tobacco Products An approximately 0.4 g sample of each tobacco product is collected and the bacterial DNA is extracted using, for example, the UltraClean Soil DNA Isolation Kit (MoBio Laboratories, Carlsbad, CA) according to the manufacturer's instructions. The DNA is quantified and used as a template for PCR reactions to amplify the V1/V2 and V6 variable regions of the 16S rRNA genes.

To amplify the V1/V2 16S rRNA region, PCR reactions are prepared with the purified DNA, PCR master mix and associated primers. To amplify the V1N2, one set of primers is used that contain 454-specific adaptors, linker nucleotides, a unique base barcode, and the specific V1/V2 bacterial primers. The PCR reactions are carried out according to standard protocols. The PCR reactions are quantified using a PicoGreen assay (Invitrogen, Carlsbad, CA) and the reaction products pooled in equimolar amounts of PCR products for, for example, 454 LifeSciences Titanium sequencing.

To amplify the V6 regions, PCR reactions are carried out using the multiplex sets of primers. The sets include 5 forward and 4 reverse primers containing 454-specific adaptors, linker nucleotides, a unique 6 base barcode, and the specific V6 bacterial primers. The PCR reactions are carried out as previously described. The PCR reactions are quantified, pooled and sequenced as described above for the V1/V2 region.

Following the sequencing runs, the DNA sequence data are checked for quality and the pooled sequence runs are then sorted based on their unique barcode and primer sequences. The sorted sequence flowgram files are analyzed with, for example, MG-RAST, and converted to FASTQ format. The taxonomic identifications are performed using MG-RAST's Best Hit Classification algorithm to compare sequences to the GreenGenes databases to determine the number of sequences corresponding to specific operational taxonomic units (OTU) for each of the STPs. The resultant OTU data (numbers of sequence reads per OTU) are exported to determine the relative percentages of the different taxa present in each sample. Sample populations are evaluated in MG-RAST, rarefaction curves are generated and subsequent alpha diversity (for example, Shannon diversity) calculated to evaluate the population composition of each sample. Principal Coordinate Analysis (PCoA) is carried out in MG-RAST and phylogenetic analysis using the Euclidean distance algorithm are used to evaluate population differences between the samples at the Class level.

Denaturing Gradient Gel Electrophoresis (DGGE). DGGE is used to evaluate potential changes in the bacterial population in the STPs (smokeless tobacco products) over the sampling period. Total bacterial DNA is isolated from each tobacco sample, using the UltraClean Soil DNA Isolation Kit, and the DNA concentration is quantified. Isolated DNA is stored at −80° C. to facilitate normalization of DNA concentrations across all samples (days 1, 3, 5, 8 and 15) for a particular STP. For each of the DNA samples for a product, the DNA concentrations are normalized and subjected to PCR using a common master mix. The V3 region of the 16S rRNA gene is amplified. The DNA concentrations of the PCR reaction products are normalized and 500 ng of each sample from a particular tobacco product are separated on a single gel using denaturing conditions. This approach, including each of the time point samples from each tobacco product on a single gel, allows detection of potential changes in the microbial populations over the sampling period. The DGGE gels are stained and digitally photographed. Banding patterns are compared to identify changes in band position and intensity, which indicate population changes.

That which is claimed:

1. A method of reducing the level of at least one nitrate-reducing bacterium on a harvested tobacco plant, plant part, or plant cell, the method comprising the steps of:

applying to the harvested tobacco plant, plant part, or plant cell a solution comprising a genetically modified bacterium comprising a heterologous nucleic acid molecule comprising a nucleic acid sequence encoding an endolysin, wherein the nucleic acid sequence is operably linked to a promoter active in the genetically modified bacterium, wherein the genetically modified bacterium expresses the endolysin, and wherein the expressed endolysin reduces the level of at least one nitrate-reducing bacterium on the harvested tobacco plant, plant part, or plant cell as compared to the level of the at least one nitrate-reducing bacterium on a control harvested tobacco plant, plant part, or plant cell not having the genetically modified bacterium applied thereto.

2. The method of claim 1, wherein the genetically modified bacterium is a nitrite sink and/or has a nitrite reductase gene.

3. The method of claim 1, wherein the genetically modified bacterium is a lactic acid bacterium.

4. The method of claim 1 further comprising,
producing a tobacco product from the harvested tobacco plant, plant part, or plant cell.

5. The method of claim 4, wherein the level of at least one tobacco specific nitrosamine (TSNA) in the tobacco product is at least 10% lower than the level of the at least one TSNA in a control harvested tobacco product produced without applying the genetically modified bacterium thereto.

6. The method of claim 4, wherein the level of nitrite in the tobacco product is reduced as compared to the level of nitrite in a control harvested tobacco product produced without applying the genetically modified bacterium thereto.

7. The method of claim 1, wherein the level of at least one tobacco specific nitrosamine (TSNA) in the harvested tobacco plant, plant part, or plant cell is at least 10% lower than the level of the at least one TSNA in a control harvested tobacco plant, plant part, or plant cell not having the genetically modified bacterium applied thereto.

8. The method of claim 1, wherein the level of nitrite in the harvested tobacco plant, plant part, or plant cell is reduced as compared to the level of nitrite in a control harvested tobacco plant, plant part, or plant cell not having the genetically modified bacterium applied thereto.

9. The method of claim 1, further comprising a step of curing and/or fermenting the harvested tobacco plant, plant part, or plant cell.

* * * * *